United States Patent [19]

Hain et al.

[11] Patent Number: 5,292,328
[45] Date of Patent: Mar. 8, 1994

[54] POLYPROPYLENE MULTIFILAMENT WARP KNITTED MESH AND ITS USE IN SURGERY

[75] Inventors: Matthew E. Hain, New Haven; Cheng-Kung Liu, Norwalk, both of Conn.

[73] Assignee: United States Surgical Corporation, Norwalk, Conn.

[21] Appl. No.: 780,857

[22] Filed: Oct. 18, 1991

[51] Int. Cl.$^5$ .............................................. A61B 17/00
[52] U.S. Cl. ................................. 606/151; 264/210.8; 264/211.17; 264/211.2; 264/211.24; 604/365; 428/361
[58] Field of Search ...................... 606/151, 230, 231; 264/211.22, 211.24, 210.8, 211.4, 211.17, 211.2; 428/394, 378, 374, 361; 604/365

[56] References Cited

U.S. PATENT DOCUMENTS

| | | |
|---|---|---|
| 3,054,406 | 9/1962 | Usher . |
| 3,124,136 | 3/1964 | Usher . |
| 3,463,158 | 8/1969 | Schmitt et al. . |
| 3,874,376 | 4/1975 | Dart et al. ................................. 602/8 |
| 4,008,303 | 2/1977 | Glick et al. ............................ 264/78 |
| 4,193,137 | 3/1980 | Heck . |
| 4,347,206 | 8/1982 | Roberts ........................... 264/211.15 |
| 4,347,847 | 9/1982 | Usher . |
| 4,452,245 | 6/1984 | Usher . |
| 4,491,657 | 1/1985 | Saito et al. ...................... 264/211.15 |
| 4,520,821 | 6/1985 | Schmidt et al. . |
| 4,633,873 | 1/1987 | Duminican et al. . |
| 4,652,264 | 3/1987 | Duminican . |
| 4,655,221 | 4/1987 | Devereux . |
| 4,755,184 | 6/1988 | Silverberg . |
| 4,769,038 | 9/1988 | Bendavid et al. ...................... 623/13 |
| 4,838,884 | 6/1989 | Duminican et al. . |
| 4,863,472 | 9/1989 | Törmälä et al. . |
| 5,002,551 | 3/1991 | Linsky et al. . |
| 5,180,375 | 1/1993 | Feibus ................................. 604/264 |

FOREIGN PATENT DOCUMENTS

| | | |
|---|---|---|
| 0101650 | 8/1983 | European Pat. Off. . |
| 334046 | 9/1989 | European Pat. Off. . |

OTHER PUBLICATIONS

European Search Reported Realted to 07/780,857.
Wantz, "Atlas of Hernia Surgery", Raven Press, New York, 1991.

*Primary Examiner*—Stephen C. Pellegrino
*Assistant Examiner*—Gary Jackson

[57] ABSTRACT

A surgical mesh of warp knit construction is fabricated from a polypropylene multifilament yarn.

13 Claims, No Drawings

POLYPROPYLENE MULTIFILAMENT WARP KNITTED MESH AND ITS USE IN SURGERY

BACKGROUND OF THE INVENTION

This invention relates to a textile material and, in particular, to a nonabsorbable surgical mesh of warp knit construction fabricated from a polypropylene multifilament yarn.

Knitted and woven fabrics constructed from a variety of synthetic fibers and the use of the fabrics in surgical repair are known from, among others, U.S. Pat. Nos. 3,054,406; 3,124,136; 4,193,137; 4,347,847; 4,452,245; 4,520,821; 4,633,873; 4,652,264; 4,655,221,; 4,838,884; 5,002,551; and, European Patent Application No. 334,046.

Hernia repairs are among the more common surgical operations which employ a mesh fabric prothesis. A mesh constructed from polypropylene monofilament, while it induces a good fibroblastic response ensuring its prompt fixation and integration with tissue at the surgical repair site, is considered to be too stiff for some types of hernioplasties, e.g., giant prosthetic reinforcement of the visceral sac (GPRVS). While a warp knitted surgical mesh constructed from a nonabsorbable polyester multifilament yarn (e.g., Mersilene of Ethicon, Inc.) has been indicated to be a particularly desirable prosthesis for a GPRVS procedure due to its suppleness and elasticity (Wantz, "Atlas of Hernia Surgery", Raven Press, 1991, p. 102), were it not for the aforementioned stiffness associated with a polypropylene monofilament mesh, the later would likely be the material of choice due to its greater strength and chemical inertness.

SUMMARY OF THE INVENTION

It is an object of the present invention to provide a surgical mesh fabricated from polypropylene multifilament yarn which exhibits an appreciably greater flexibility than a surgical mesh constructed from polypropylene monofilament.

It is another object of the invention to provide a polypropylene multifilament warp knitted surgical mesh exhibiting a flexibility which is at least comparable to that of a nonabsorbable polyester multifilament surgical mesh of similar construction but possessing greater mechanical strength than the latter.

It is yet another object of the invention to provide a surgical mesh with a color pattern which facilitates the orientation and/or installation of the mesh at a surgical repair site.

Another specific object of the invention is the provision of a thermoplastic surgical mesh which is cut to size with an ultrasonic slitter.

Still another specific object of the invention is the provision of a surgical mesh coated on one side with a material that prevents or minimizes organ adhesions.

In keeping with these and other objects of the invention, there is provided a warp knitted surgical mesh fabricated from polypropylene multifilament yarn.

The foregoing mesh is considerably more flexible than any of the known surgical mesh materials constructed from monofilament. Thus, e.g., the mesh of this invention can be more easily passed through a trocar and into a body cavity. The greater flexibility of the mesh makes it more maneuverable and easier to be installed at the desired surgical site than a monofilament mesh of otherwise similar construction. Compared to a nonbioabsorbable surgical mesh knitted from polyester multifilament yarn, the polypropylene multifilament mesh of this invention possesses much greater strength but at no loss of flexibility and suppleness.

The mesh of this invention finds application in a number of surgical procedures including the repair of hernias, anatomical defects of the abdominal wall, diaphragm, and chest wall, correction of defects in the genitourinary system, repair of traumatically damaged organs such as the spleen, liver or kidney, and so forth.

DESCRIPTION OF THE PREFERRED EMBODIMENTS

The surgical mesh of this invention is fabricated from a yarn formed from a polypropylene resin (isotactic index of at least about 90), preferably one which is already accepted for use as a suture material, e.g., a polypropylene resin having a melt flow index in g/10 min (ASTM D 1231-82) of from about 2 to about 6, preferably from about 2.1 to about 5.0 and most preferably from about 2.5 to about 4.6.

Known and conventional apparatus and procedures can be used for the production of polypropylene multifilament yarns from which the mesh of this invention is constructed. Properties of the individual polypropylene filaments and the yarns manufactured therefrom are advantageously as set forth in Table I below:

TABLE I
PROPERTIES OF MONOFILAMENTS AND YARNS CONSTRUCTED THEREFROM

|  | Broad Range | Preferred Range | Most Preferred Range |
|---|---|---|---|
| Denier per Filament | 0.5–6 | 1–4 | 2–3 |
| Filaments per Yarn | 10–60 | 20–40 | 25–35 |
| Denier per Yarn | at least 10 | 40–80 | 50–70 |

During the spinning process, after the individual polypropylene filaments have been brought together to provide the yarn, it is conventional practice to apply a spin finish to the yarn. The spin finish typically contains lubricant, antistatic and adhesive components to hold the yarn together and improve its processability, e.g., drawability. One spin finish composition which is known to provide generally good results is Lurol 1187 (Goulston Inc., 700 N. Johnson Street, Monroe, N.C. 28110) which can be applied to the yarn from solution prepared with a suitable solvent, e.g., as a 5–35 weight percent solution in isopropyl alcohol.

Following spinning, the multifilament yarn is ordinarily subjected to further mechanical processing, e.g., twisting, air entanglement, etc., in order to further enhance its processability. Thus, e.g., the yarn can be ring twisted at a rate of from about 1 to about 5 turns per inch or air entangled at a level of at least about 50 nodes per meter prior to being knitted into mesh.

In a preferred melt spinning process for obtaining yarn to be knitted into the surgical mesh of this invention, the isotactic polypropylene resin, melt spinning equipment and ranges of operating conditions set forth below in Table II can be advantageously employed:

TABLE II: MELT SPINNING OF POLYPROPYLENE MULTIFILAMENT YARNS

A. Polypropylene Resin

The preferred polypropylene resin is a surgical suture grade resin having an isotactic index of about 95 or greater and a melt flow rate of from about 2.5 to about 4.6.

B. Melt Spinning Apparatus and Operating Conditions

| Apparatus Component, Operating Parameter | Range of Operating Condition |
| --- | --- |
| Extruder barrel temp., zone 1 °C. | 230–250 |
| Extruder barrel temp., zone 2 °C. | 230–270 |
| Extruder barrel temp., zone 3 °C. | 230–270 |
| Extruder barrel pressure, psi | 1000–2000 |
| Extruder barrel melt temp., °C. | 230–275 |
| Pump size, cc per rev. | .16–.584 |
| Pump rpm | 25–35 for size .16 pump<br>6–10 for size .584 pump |
| Pump temp., °C. | 220–250 |
| Pump pressure, psi | 400–1000 |
| Pump melt temp., °C. | 215–255 |
| Block temp., °C. | 220–250 |
| Clamp temp., °C. | 220–250 |
| Adapter temp., °C. | 220–250 |
| Candle filter, screen, microns | 10–100 |
| No. of spinneret orifices | 10–200 |
| Diameter of spinneret orifices, .001 in | 5–30 |
| Spinneret temp., °C. | 220–250 |
| Spinneret pressure, psi | 400–1500 |
| Spinneret melt temp., °C. | 215–255 |
| cc/hr output, per spinneret orifice | 5–20 |
| First pair of godets, °C. | 40–90 |
| First pair of godets, mpm | 100–300 |
| Second pair of godets, °C. | 70–130 |
| Second pair of godets, mpm | 300–1000 |
| Draw (stretch) ratio | 2–4 |
| Third pair of godets, °C. | ambient |
| Third pair of godets, mpm | 250–1000 |
| Shrinkage (relaxation), percent | 5–15 |

C. Properties of Individual Filaments and Polypropylene Yarns Obtained Therefrom

| Property | Range of Property |
| --- | --- |
| Denier per Filament | .3–20 |
| Filaments per Yarn | 10–200 |
| Denier per Yarn | 3–300 |

The surgical mesh of this invention can be fabricated from these and similar multifilament polypropylene yarns employing known and conventional warp knitting apparatus and techniques, e.g., the tricot and Raschel knitting machines and procedures described in "Warp Knitting Production" by Dr. S. Raz, Melliand Textilberichte GmbH, Rohrbacher Str. 76, D-6900 Heidelberg, Germany (1987), the contents of which are incorporated by reference herein. As is well known in the art of warp knitting, the number of courses and wales per inch in a knitted material is affected by a number of machine operating variables such as the rate at which the fabric is drawn away from the needles, the number of needles per inch, the amount of tension applied to the warp yarns and other variables after the fabric leaves the machine, e.g., the heat setting conditions.

The structure of the knitted mesh of this invention can be defined for any given yarn in terms of the number of courses and wales per inch and the knit design for which there can be a great number of variations. Advantageously, the polypropylene multifilament yarns of Table II can be warp knitted, preferably tricot knitted on a 2 bar set-up, to provide surgical meshes possessing the structural characteristics set forth in Table III as follows:

TABLE III
STRUCTURAL CHARACTERISTICS OF SURGICAL MESHES

| | Broad Range | Preferred Range | Most Preferred Range |
| --- | --- | --- | --- |
| Courses per Inch | 20–80 | 25–60 | 30–50 |
| Wales per Inch | 12–40 | 18–34 | 20–24 |

Following knitting, the mesh is cleaned to remove the spin finish and thereafter heat set to stabilize the fabric. For the latter operation, the mesh can be secured to a tenter frame which maintains the mesh at a predetermined width, the frame then being passed through an elongate heating zone at a temperature of from about 120° to about 180° C., preferably at a temperature of from about 120° to about 150° C., at a rate providing a dwell time of from about 10 to about 55 seconds and preferably from about 20 to about 50 seconds. On a smaller scale, the mesh can be mounted upon a stationary frame which is then placed in an oven for about 5 to about 12 minutes at from about 125° to about 140° C. Following heat setting, the mesh is cut to size, packaged and sterilized.

The mesh can be cut to any desired configuration, e.g., a square or rectangular shape, of appropriate dimensions. Two suitable configurations are a square of 4 inches and a rectangle measuring 9 inches by 14 inches. In cutting the mesh to size, it has been found advantageous to employ an ultrasonic slitter or cutter, various types of which are commercially available. Unlike the result one obtains when cutting with a blade, i.e., frayed yarn ends, or when the yarn ends are heat-sealed, i.e., bead-like formations, cutting the mesh to size with an ultrasonic cutter avoids both frayed and beaded ends.

The polypropylene multifilament warp knitted mesh of this invention possesses a ball burst strength (ASTM D 3787-80A) of at least about 50 kg, preferably at least about 50 kg and most preferably at least about 80 kg. Even at only 50 kg ball burst strength, the mesh of this invention is considerably stronger, e.g., up to 100 percent stronger, than a nonabsorbable polyester multifilament warp knitted mesh of otherwise comparable construction.

For some applications, particularly those involving laparoscopic procedures, it may be desirable to partially stiffen the mesh so that the mesh can be rolled up for easy passage through a trocar and into a body cavity and once inside the body, spring back to its previous flattened condition. One way of accomplishing this partial stiffening effect is to coat the mesh with a polymer such as poly(hydroxymethyl methacrylate). The amount of polymer applied to the mesh to achieve a particular stiffening effect can, of course, be determined employing simple and routine experimentation. Stiffening can also be achieved by heating the mesh at a temperature which is higher and/or for a period of time which is longer than the aforementioned heat setting conditions. Thus, heating at from about 160° to about 180° C. for from about 30 minutes to about 2 hours will cause the mesh to stiffen.

It can also be advantageous to provide the surgical mesh of this invention with a clearly visible color pattern, e.g., in the form of a grid of two differently colored yarns such as dark blue and light blue, dark blue or light blue and clear or natural, etc., as such a pattern will tend to facilitate the proper orientation and/or installation of the mesh at the surgical repair site. The mesh can contain yarn of one color in the machine direction, yarn of the other color being incorporated into the mesh fabric after knitting. In the case where the mesh is manufactured on a weft insertion warp knitter, both the knitting and the insertion of the weft can be accomplished in a single operation.

The following example is illustrative of the surgical mesh of this invention and its fabrication.

EXAMPLE

The surgical mesh of this invention was manufactured from a 96 percent isotactic polypropylene having a melt flow index of about 3.3 g/10 min, a weight average molecular weight of 283,000 and a number average weight of 61,000 as reported by the supplier (Resin F040A Natural of Aristech Chemical Corporation, Pittsburgh, Pa.).

The conditions of melt spinning the polypropylene multifilament yarn, warp knitting the yarn to provide the surgical mesh and the properties of the mesh and its heat setting conditions are set forth in Table IV below:

TABLE IV
SURGICAL MESH MANUFACTURING CONDITIONS

A. Melt Spinning Apparatus and Operating Conditions

| Apparatus Component, Operating Parameter | Operating Condition |
|---|---|
| Extruder barrel temp., zone 1 °C. | 240 |
| Extruder barrel temp., zone 2 °C. | 260 |
| Extruder barrel temp., zone 3 °C. | 260 |
| Extruder barrel pressure, psi | 1500 |
| Extruder barrel melt temp., °C. | 260 |
| Pump size, cc per rev. | 0.16 |
| Pump rpm | 32 |
| Pump temp., °C. | 240 |
| Pump pressure, psi | 500-750 |
| Pump melt temp., °C. | 240 |
| Block temp., °C. | 240 |
| Clamp temp., °C. | 240 |
| Adapter temp., °C. | 240 |
| Candle filter, screen, microns | 40 |
| No. of spinneret orifices | 30 |
| Diameter of spinneret orifices, .001 in | 10 |
| Spinneret temp., °C. | 240 |
| Spinneret pressure, psi | 400-800 |
| Spinneret melt temp., °C. | 240 |
| cc/hr output, per spinneret orifice | 10.2 |
| First pair of godets, °C. | 65 |
| First pair of godets, mpm | 160 |
| Second pair of godets, °C. | 90 |
| Second pair of godets, mpm | 510 |
| Draw (stretch) ratio | 2.9 |
| Third pair of godets, °C. | ambient |
| Third pair of godets, mpm | 465 |
| Shrinkage (relaxation), percent | 9 |
| Spin Finish | 35 wt % isopropyl alcohol solution of Lurol 1187, as needed |

B. Properties of Polypropylene Multifilament Yarn

| | |
|---|---|
| Denier per Filament: | 2 |
| Filaments per Yarn: | 30 |
| Denier per Yarn: | 60 |

C. Tricot Knitting Conditions

| | | |
|---|---|---|
| Knitting Machine: | 20 gauge (20 needle) 2-bar tricot knitter (Mayer Textile Machine Corporation, Clifton, NJ) | |
| Courses per Inch: | 40 | |
| Wales per Inch: | 22 | |
| Knit Design: | Back Bar | Front Bar |
| | 1/0 | 0/1 |
| | 4/5 | 1/0 |

TABLE IV-continued
SURGICAL MESH MANUFACTURING CONDITIONS

D. Properties of the Surgical Mesh

| | |
|---|---|
| Fabric Width: | 48 inches |
| Fabric Weight: | 2.5-2.8 oz./sq. yd. |
| Ball Burst Strength: | 58 kg |

The mesh was heat set by being clamped to a frame and placed in an oven heated to 130° C. for 10 minutes.

What is claimed is:

1. A warp knitted surgical mesh fabricated from polypropylene multifilament yarn, the polypropylene being an isotactic polypropylene resin having a melt flow index, g/10 min, of from about 2 to about 6, the yarn possessing a denier of at least about 10 and being constructed with from about 10 to about 60 filaments each having a denier of from about 0.5 to about 6, the mesh possessing from about 20 to about 80 courses per inch and from about 12 to about 40 wales per inch, the yarn being produced by the process which comprises melt spinning the polypropylene employing an extruder equipped with a spinneret and downstream of the extruder a draw frame possessing three pairs of godets, the extruder being operated in one or more zones thereof at a temperature of from about 230° to about 270° C., the pressure of the extruder being from about 1000 to about 2000 psi, the temperature of the spinneret being from about 220° to about 250° C., the first pair of godets being operated at a temperature of from about 50° to about 90° C. and an mpm of from about 100 to about 300, the second godet being operated at a temperature of from about 70° to about 130° C. and an mpm of from about 300 to about 1000 and the third godet being operated at ambient temperature and an mpm of from about 250 to about 1000, the draw ratio of the yarn being from about 2 to about 4 and the shrinkage of the yarn being from about 5 to about 15 percent.

2. The surgical mesh of claim 1 wherein the polypropylene is an isotactic polypropylene resin having a melt flow index, g/10 min, of from about 2.1 to about 5.0.

3. The surgical mesh of claim 1 wherein the polypropylene is an isotactic polypropylene resin having a melt flow index, g/10 min, of from about 2.5 to about 4.0.

4. The surgical mesh of claim 1 wherein the yarn is made from filaments of from about 1 to about 4 denier, the yarn is constructed with from about 20 to about 40 filaments and the yarn possesses a denier of from about 40 to about 80.

5. The surgical mesh of claim 1 wherein the yarn is made from filaments of from about 2 to about 3 denier, the yarn is constructed with from about 25 to about 35 filaments and the yarn possesses a denier of from about 50 to about 70.

6. The surgical mesh of claim 1 wherein the mesh possesses from about 25 to about 60 courses per inch and from about 18 to about 32 wales per inch.

7. The surgical mesh of claim 1 wherein the mesh possesses from about 25 to about 60 courses per inch and from about 18 to about 34 per inch.

8. The surgical mesh of claim 1 exhibiting a color pattern to facilitate its orientation and/or installation at a surgical repair site.

9. The surgical mesh of claim 1 wherein said surgical mesh is heated to provide a heat set.

10. The surgical mesh of claim 1 coated with poly(hydroxymethacrylate) for enhanced stiffness compared to the stiffness of the uncoated mesh.

11. The surgical mesh of claim 1 heated to a temperature and for a duration resulting in enhanced stiffness compared with the stiffness of the mesh prior to being heated.

12. The surgical mesh of claim 1 cut to size by ultrasonic cutting, the cut ends of the yarns being sealed but unbeaded.

13. A surgical mesh fabricated from polypropylene, the mesh being subjected to a stiffening treatment which enhances the stiffness of the mesh compared with the stiffness of the mesh prior to the stiffening treatment, wherein the stiffening treatment comprises heating the mesh to a temperature from about 160° to about 180° C. for about 30 minutes to about two hours and applying poly(hydroxymethyl methacrylate) as a mesh stiffening substance.

* * * * *